(12) United States Patent
Wang et al.

(10) Patent No.: US 7,585,899 B2
(45) Date of Patent: Sep. 8, 2009

(54) CATALYST STRUCTURE AND METHOD OF FISCHER-TROPSCH SYNTHESIS

(75) Inventors: Yong Wang, Richland, WA (US); David P. Vanderwiel, Richland, WA (US); Anna Lee Y. Tonkovich, Pasco, WA (US); Yufei Gao, Kennewick, WA (US); Eddie G. Baker, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 11/364,595

(22) Filed: Feb. 27, 2006

(65) Prior Publication Data

US 2006/0148910 A1 Jul. 6, 2006

Related U.S. Application Data

(60) Continuation of application No. 10/666,430, filed on Sep. 19, 2003, now Pat. No. 7,045,486, which is a division of application No. 10/038,228, filed on Jan. 3, 2002, now Pat. No. 6,660,237, which is a division of application No. 09/375,610, filed on Aug. 17, 1999, now Pat. No. 6,451,864.

(51) Int. Cl.
*C07C 27/00* (2006.01)
(52) U.S. Cl. .................................. 518/700; 518/715
(58) Field of Classification Search ............ 518/700, 518/715
See application file for complete search history.

(56) References Cited

U.S. PATENT DOCUMENTS

| | | | |
|---|---|---|---|
| 4,738,948 A | 4/1988 | Iglesia et al. | |
| 4,795,618 A | 1/1989 | Laumen et al. | |
| 4,801,620 A | 1/1989 | Fujitani et al. | |
| 4,833,170 A | 5/1989 | Agee | |
| 4,992,406 A | 2/1991 | Mauldin et al. | |
| 5,126,377 A * | 6/1992 | Bessell ........................ 518/714 |
| 5,227,407 A | 7/1993 | Kim | |
| 5,366,719 A | 11/1994 | van Wingerden et al. | |
| 5,545,674 A | 8/1996 | Behrmann et al. | |
| 5,652,193 A | 7/1997 | Herskowitz | |
| 5,811,062 A | 9/1998 | Wegeng et al. | |
| 6,159,358 A | 12/2000 | Mulvaney et al. | |
| 6,180,842 B1 | 1/2001 | Berlowitz et al. | |
| 6,211,255 B1 | 4/2001 | Schanke et al. | |
| 6,262,131 B1 | 7/2001 | Arcuri et al. | |
| 6,265,451 B1 | 7/2001 | Zhou et al. | |
| 6,319,960 B1 | 11/2001 | Behrmann et al. | |
| 6,451,864 B1 | 9/2002 | Wang et al. | |
| 6,491,880 B1 | 12/2002 | Wang et al. | |
| 6,558,634 B1 | 5/2003 | Wang et al. | |
| 6,616,909 B1 * | 9/2003 | Tonkovich et al. ........ 423/648.1 |
| 6,660,237 B2 | 12/2003 | Wang et al. | |
| 6,680,044 B1 | 1/2004 | Tonkovich et al. | |
| 6,749,814 B1 * | 6/2004 | Bergh et al. .................. 422/130 |
| 6,749,817 B1 | 6/2004 | Mulvaney et al. | |
| 6,750,258 B2 | 6/2004 | Wang et al. | |
| 6,982,287 B2 | 1/2006 | Wang et al. | |
| 7,045,486 B2 | 5/2006 | Wang et al. | |

FOREIGN PATENT DOCUMENTS

| | | |
|---|---|---|
| EP | 0869842 | 10/1998 |
| WO | WO 98/38147 | 9/1998 |
| WO | WO 01/51194 | 7/2001 |
| WO | WO 03/033134 | 4/2003 |

OTHER PUBLICATIONS

Bergh et al., U.S. Appl. No. 60/122,704, filed Mar. 1999.

* cited by examiner

*Primary Examiner*—Jafar Parsa
(74) *Attorney, Agent, or Firm*—Derek H. Maughan; Frank Rosenberg

(57) ABSTRACT

The present invention includes a catalyst structure and method of making the catalyst structure for Fischer-Tropsch synthesis that both rely upon the catalyst structure having a first porous structure with a first pore surface area and a first pore size of at least about 0.1 μm, preferably from about 10 μm to about 300 μm. A porous interfacial layer with a second pore surface area and a second pore size less than the first pore size is placed upon the first pore surface area. Finally, a Fischer-Tropsch catalyst selected from the group consisting of cobalt, ruthenium, iron and combinations thereof is placed upon the second pore surface area. Further improvement is achieved by using a microchannel reactor wherein the reaction chamber walls define a microchannel with the catalyst structure placed therein through which pass reactants. The walls may separate the reaction chamber from at least one cooling chamber. The present invention also includes a method of Fischer-Tropsch synthesis.

41 Claims, 2 Drawing Sheets

CATALYST STRUCTURE AND METHOD OF FISCHER-TROPSCH SYNTHESIS

RELATED APPLICATIONS

This is a continuation of U.S. patent application Ser. No. 10/666,430, now U.S. Pat. No. 7,045,486, filed Sep. 19, 2003 which was a divisional of U.S. patent application Ser. No. 10/038,228, now U.S. Pat. No. 6,660,237, filed Jan. 3, 2002 which was a divisional of U.S. patent application Ser. No. 09/375,610, now U.S. Pat. No. 6,451,864, filed Aug. 17, 1999.

FIELD OF THE INVENTION

The present invention is a catalyst structure and method of making, and a method of Fischer-Tropsch synthesis.

BACKGROUND OF THE INVENTION

Fischer-Tropsch synthesis is carbon monoxide hydrogenation that is usually performed on a product stream from another reaction including but not limited to steam reforming (product stream $H_2/CO\sim3$), partial oxidation (product stream $H_2/CO\sim2$), autothermal reforming (product stream $H_2/CO\sim2.5$), $CO_2$ reforming ($H_2/CO\sim1$) coal gassification (product stream $H_2/CO\sim1$) and combinations thereof.

Fundamentally, Fischer-Tropsch synthesis has fast surface reaction kinetics. However, the overall reaction rate is severely limited by heat and mass transfer with conventional catalysts or catalyst structures. The limited heat transfer together with the fast surface reaction kinetics may result in hot spots in a catalyst bed. Hot spots favor methanation. In commercial processes, fixed bed reactors with small internal diameters or slurry type and fluidized type reactors with small catalyst particles (>50 μm) are used to mitigate the heat and mass transfer limitations. In addition, Fischer-Tropsch reactors are operated at lower conversions per pass to minimize temperature excursion in the catalyst bed. Because of the necessary operational parameters to avoid methanation, conventional reactors are not improved even with more active Fischer-Tropsch synthesis catalysts. Detailed operation is summarized in Table 1 and FIG. 1.

TABLE 1

Comparison of Residence Times Effects in Fischer-Tropsch Experimentation

| Ref[A] | Catalyst | Conditions | Residence time | Conversion | $CH_4$ selectivity |
|---|---|---|---|---|---|
| 1 | Co/ZSM-5 | 240° C., 20-atm, $H_2/CO = 2$ | 3.6-sec | 60% | 21% |
| 2 | Co/MnO | 220° C., 21-atm, $H_2/CO = 2$ | 0.72-sec | 13% | 15% |
| 3 | Co—Ru/$TiO_2$ | 200° C., 20-atm, $H_2/CO = 2$ | 3-sec | 61% | 5% |
|  | Co/$TiO_2$ | " | 8-sec | 49% | 7% |
| 4 | Co/$TiO_2$ | 200° C., 20-atm, $H_2/CO = 2.1$ | 2-sec | 9.5% | ~9% |
|  |  | " | 12-sec | 72% | ~6% |
| 5 | Ru/$Al_2O_3$ | 222° C., 21-atm, $H_2/CO = 3$ | 4.5-sec | 20% | ? |
|  |  | " | 7.2-sec | 36% |  |
|  |  | " | 8.4-sec | 45% |  |
|  |  | " | 9.6-sec | 51% |  |
|  |  | " | 12-sec | 68% |  |
|  |  | " | 14-sec | 84% |  |
| 6 | Ru/$Al_2O_3$ | 250° C., 22-atm, $H_2/CO = 2$ | 7.2-sec | 38% | 5% |
| 7 | Ru/$Al_2O_3$ | 225° C., 21-atm, $H_2/CO = 2$ | 12-sec | 66% | 13% |
|  |  | 222° C., 21-atm, $H_2/CO = 3$ | 12-sec | 77% | 34% |

For references that contained results for multiple experimental conditions, the run which best matched our conversion, selectivity and/or conditions was chosen for comparison of residence time.
(A) References
1. Bessell, S., Appl. Catal. A: Gen. 96, 253 (1993).
2. Hutchings, G. J., Topics Catal. 2, 163 (1995).
3. Iglesia, E., S. L. Soled and R. A. Fiato (Exxon Res. and Eng. Co.), U.S. Pat. No. 4,738,948, Apr. 19, 1988.
4. Iglesia, E., S. C. Reyes, R. J. Madon and S. L. Soled, Adv. Catal. 39, 221 (1993).
5. Karn, F. S., J. F. Shultz and R. B. Anderson, Ind. Eng. Chem. Prod. Res. Dev. 4(4), 265 (1965).
6. King, F., E. Shutt and A. I. Thomson, Platinum Metals Rev. 29(44), 146 (1985).
7. Shultz, J. F., F. S. Karn and R. B. Anderson, Rep. Invest. - U.S. Bur. Mines 6974, 20 (1967).

Literature data (Table 1 and FIG. 1) were obtained at lower $H_2/CO$ ratio (2:1) and longer residence time (3 sec or longer). Low $H_2/CO$ (especially 2-2.5), long residence time, low temperature, and higher pressure favor Fischer-Tropsch synthesis. Selectivity to $CH_4$ can be significantly increased by increasing $H_2/CO$ ratio from 2 to 3. Increasing residence time also has a dramatic favorable effect on the catalyst performance. Although reference 3 in Table 1 shows satisfactory results, the experiment was conducted under the conditions where Fischer-Tropsch synthesis is favored (at least 3 sec residence time, and $H_2/CO=2$). In addition, the experiment of reference 3 was done using a powdered catalyst on an experimental scale that would be impractical commercially because of the pressure drop penalty imposed by powdered catalyst. Operating at higher temperature will enhance the conversion, however at the much higher expense of selectivity to $CH_4$. It is also noteworthy that residence time in commercial Fischer-Tropsch units is at least 10 sec.

Hence, there is a need for a catalyst structure and method of Fischer-Tropsch synthesis that can achieve the same or higher conversion at shorter residence time, and/or at higher $H_2/CO$.

SUMMARY OF THE INVENTION

The present invention includes a catalyst structure and method of making the catalyst structure for Fischer-Tropsch synthesis that both rely upon the catalyst structure having a first porous structure with a first pore surface area and a first pore size of at least about 0.1 μm, preferably from about 10

μm to about 300 μm. A porous interfacial layer with a second pore surface area and a second pore size less than the first pore size is placed upon the first pore surface area. Finally, a Fischer-Tropsch catalyst selected from the group consisting of cobalt, ruthenium, iron, rhenium, osmium and combinations thereof is placed upon the second pore surface area.

Further improvement is achieved by using a microchannel reactor wherein the reaction chamber walls define a microchannel with the catalyst structure placed therein through which pass reactants. The walls may separate the reaction chamber from at least one cooling chamber.

The present invention also includes a method of Fischer-Tropsch synthesis having the steps of:
(a) providing a catalyst structure having a first porous structure with a first pore surface area and a first pore size of at least about 0.1 μm;
a porous interfacial layer with a second pore surface area and a second pore size less than the first pore size, the porous interfacial layer placed upon the first pore surface area;
a Fischer-Tropsch catalyst selected from the group consisting of cobalt, ruthenium, iron rhenium, osmium and combinations thereof placed upon the second pore surface area; and
(b) passing a feed stream having a mixture of hydrogen gas and carbon monoxide gas through the catalyst structure and heating the catalyst structure to at least 200° C. at an operating pressure, the feed stream having a residence time within the catalyst structure less than 5 seconds, thereby obtaining a product stream of at least 25% conversion of carbon monoxide, and at most 25% selectivity toward methane.

It is an object of the present invention to provide a catalyst structure for Fischer-Tropsch synthesis.

It is another object of the present invention to provide a method of Fischer-Tropsch synthesis having shorter residence time.

Advantages of the invention include (i) at residence time shorter than the prior art, higher conversions are achieved with no increase to methane selectivity; and (ii) as residence times increase, conversion increases and methane selectivity decreases (slightly). Surprisingly, the present invention represents an increase in conversion efficiency of at least a factor of 3 on the basis that equivalent conversion with conventional catalyst would require correspondingly greater residence time.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention is a catalyst structure and method of making the catalyst structure for Fischer-Tropsch synthesis which rely upon:

the catalyst is impregnated into a catalyst structure and calcined thereon. In a preferred embodiment, the catalyst structure is placed within a reaction chamber. The reaction chamber preferably has walls defining at least one microchannel through which pass reactants into the reaction chamber. The walls preferably separate the reaction chamber from at least one cooling chamber. A microchannel has a characteristic dimension less than about 1 mm.

In order to mitigate the mass transfer limitation of the catalyst structure, the catalyst impregnation forms a porous interfacial layer that is less than 50 μm, preferably less than 20 μm. Therefore, the diffusion path length is at least a factor of 5 shorter than for standard catalyst particles, and the catalyst structure is more active as indicated by the higher performance at shorter residence time. The thinner impregnated catalyst structure also enhances heat transfer, again due to the shorter heat transfer pathway, and leads to lower selectivity to $CH_4$.

In addition, because the catalyst structure is not required to be attrition resistant as would be with the catalyst particles used in a fluidized bed reactor, greater porosity may be used, for example porosity greater than about 30%. Thus mass transfer is enhanced in the catalyst structure.

The catalyst structure may be any geometric configuration including but not limited to foam, felt, wad and combinations thereof. Foam is a structure with continuous walls defining pores throughout the structure. Felt is a structure of fibers with interstitial spaces therebetween. Wad is a structure of tangled strands, like steel wool.

Figure 1:
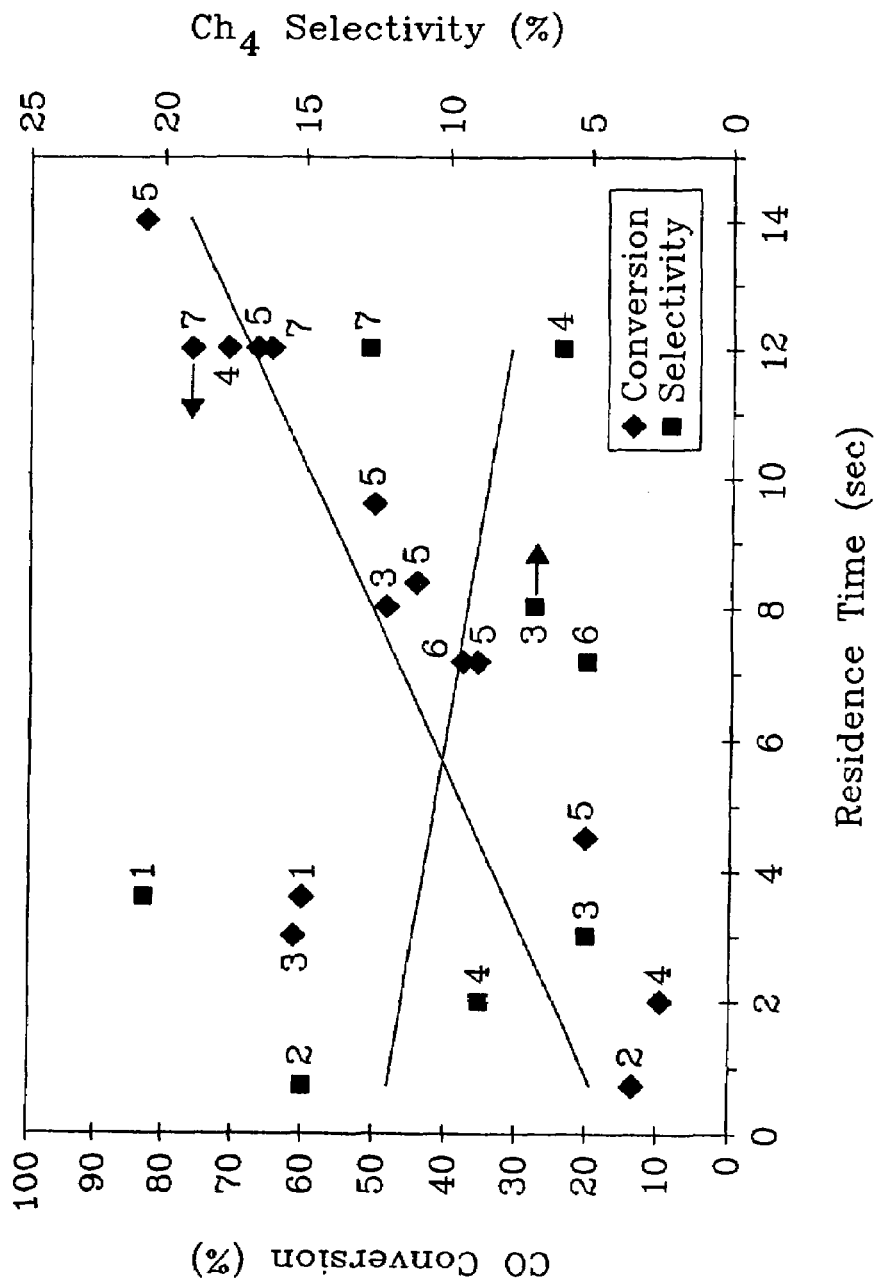
FIG. 1 is a graph of CO conversion versus residence time for prior art Fischer-Tropsch processes.
Figure 2:
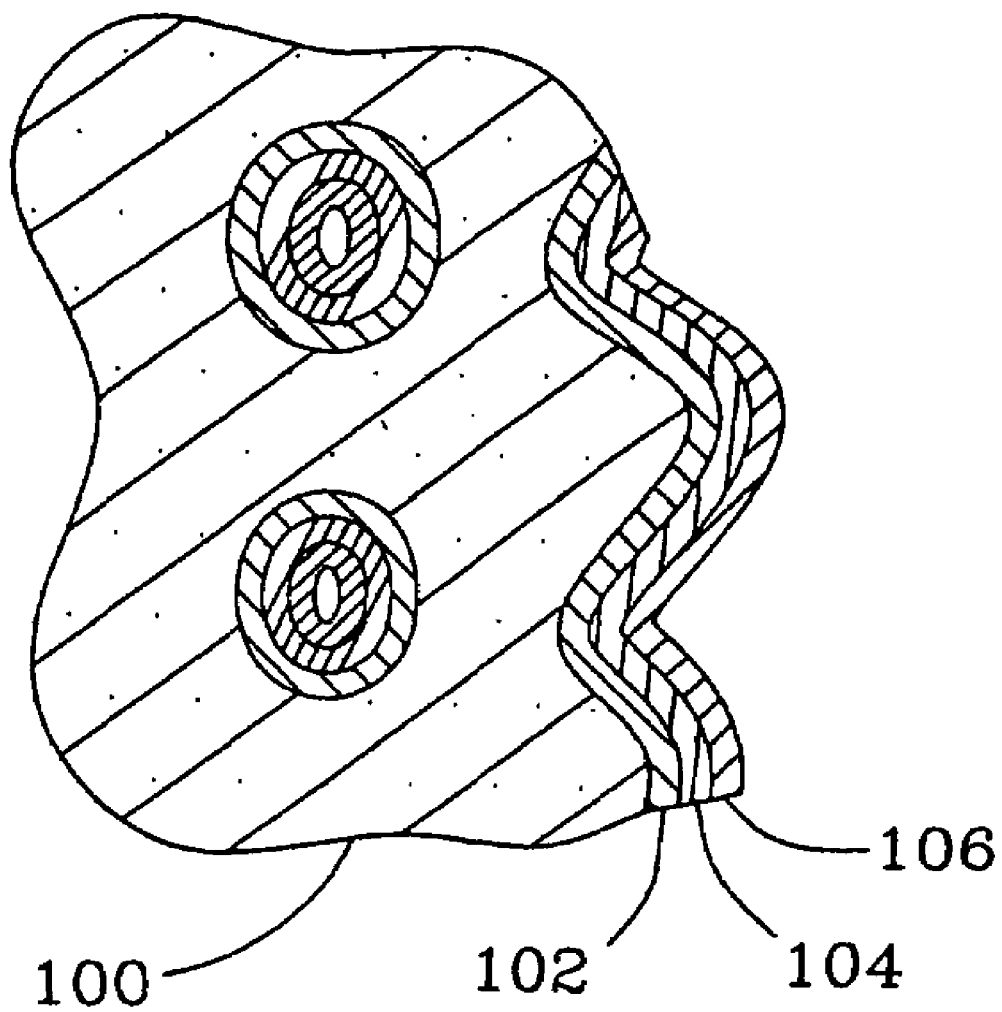
FIG. 2 is a cross section of a catalyst structure according to the present invention.

When the first porous structure is metal, its surface is passivated and coated with a ceramic layer using a chemical vapor deposition (CVD) method as described in U.S. patent application Ser. No. 09/123,781 (E-1666A) hereby incorporated by reference. The catalyst structure of the present invention is depicted in FIG. 1 having a catalyst support 100 of a first porous structure, a buffer layer 102 (optional), an interfacial layer 104, and, a catalyst or catalyst layer 106. Any layer may be continuous or discontinuous as in the form of spots or dots, or in the form of a layer with gaps or holes. Continuous layer of buffer layer 102 is preferred.

The interfacial layer 104 is a metal oxide. The metal oxide includes but is not limited to $\gamma$-$Al_2O_3$, $SiO_2$, $ZrO_2$, $TiO_2$, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. Typically the porous support 100 has a thermal coefficient of expansion different from that of the interfacial layer 104. Accordingly, for high temperature catalysis (T>150° C.) a buffer layer 102 may be needed to transition between the two coefficients of thermal expansion. Another advantage of the buffer layer 102 is avoiding side reactions such as coking or cracking caused by a bare metal foam surface. For chemical reactions which do not require large surface area supports such as catalytic combustion, the buffer layer 102 stabilizes the catalyst metal due to strong metal to metal-oxide interaction. In chemical reactions which require large surface area supports, the buffer layer 102 provides stronger bonding to the high surface area interfacial layer 104.

The buffer layer 102 is a metal oxide that is $Al_2O_3$, $TiO_2$, $SiO_2$, and $ZrO_2$ and combinations thereof. More specifically, the $Al_2O_3$ is $\alpha$-$Al_2O_3$, $\gamma$-$Al_2O_3$ and combinations thereof. The structure of the $\alpha$-$Al_2O_3$ is preferred since it is most resistant to oxygen diffusion. Therefore, it is expected that resistance against high temperature oxidation can be improved with alumina coated on the porous support 100. When the porous support 100 is metal foam, for example a stainless steel foam, a preferred embodiment has a buffer layer 102 formed of two sub-layers (not shown). The first sublayer (in contact with the porous support 100) is $TiO_2$ for good adhesion and bonding of the ceramic layers to the porous support 100. The second sublayer is $\alpha$-$Al_2O_3$ which is used for passivating the metal foam and is placed upon the $TiO_2$.

Deposition of the buffer layer 102 may be by vapor deposition including but not limited to chemical vapor deposition, physical vapor deposition or combinations thereof. Because the vapor deposition is conducted at high temperatures, polycrystalline phases are formed providing good adhesion of the metal oxide to the metal foam surface. Alternatively, the buffer layer 102 may be obtained by solution coating. For example, the solution coating has the steps of metal surface functionalization via hydroxide formation, followed by surface hydrolysis of alkoxides to obtain the polycrystalline phases. This solution coating may be preferred as a lower cost method of depositing the buffer layer 102. Polycrystalline metal oxides resist flaking of layers after several thermal cycles.

Because metal foam has web surfaces that are nonporous and smooth, deposition of the interfacial layer may be impeded. One way to mitigate this problem is to rough the metal foam surface via chemical etching. The adhesion of high surface area gamma-alumina supported metal catalysts to metal foam is significantly improved when metal foam is roughed via chemical etching using mineral acid solutions, for example HCl. Roughed web surface also shows improved resistance to the spalling of catalyst layer under thermal cyclings. The open cells of a metal foam may range from about 20 ppi (pores per inch) to about 1000 ppi and is preferably about 80 ppi.

Catalyst metals for Fischer-Tropsch synthesis include but are not limited to iron (Fe), cobalt (Co), ruthenium (Ru), rhenium (Re), osmium (Os) and combinations thereof.

The use of the catalyst impregnated metal foam permits residence time less than about 5 seconds, preferably from about 1 sec to about 2 sec. The reactor will scale up with modular reactors, which will provide at least a factor of 3 enhancement of equivalent activity.

According to the method of the present invention, residence time less than 5 seconds is achieved by: (a) providing a catalyst structure of a metal foam having a catalyst thereon; and (b) passing a feed stream having a mixture of hydrogen gas with carbon monoxide gas through the catalyst structure and heating the catalyst structure to at least 200° C., thereby obtaining a product stream of at least 25% conversion of carbon monoxide, and at most 25% selectivity toward methane. In a preferred method, the catalyst structure includes a buffer layer and an interfacial layer with the catalyst impregnated onto the interfacial layer. The ratio of hydrogen to carbon monoxide ranges from about 1:1 to about 6:1, preferably from about 2:1 to about 3.5:1.

Residence time less than 5 seconds may be accomplished with standard equipment but at the expense of significant energy to raise the space velocity of the reactants to overcome the pressure drop and poorer heat transfer leading to higher methane formation. Heat transfer from the reaction chamber is preferably enhanced by addition of microchannels on at least one reaction chamber wall on the side of the reaction chamber wall opposite the catalyst structure.

It was unexpectedly discovered that by using the catalyst structure of the present invention, reducing the pressure of the Fischer-Tropsch reaction resulted in increased yield, less selectivity toward methane.

EXAMPLE 1

A reactor was constructed with a reaction chamber with an inlet and an outlet. Internal reactor chamber dimensions were length 35.6 mm (1.4 in), height 1.5 mm (0.060 in) and width 8 mm (0.315 in).

Catalyst impregnated metal foam was made starting with a metal foam of stainless steel having a porosity of 90% as obtained from Astro Met, Cincinnati, Ohio. Foam metal surface was passivated and coated with a ceramic layer as described above.

15 wt % Co 1 wt % Ru/$\gamma$-$Al_2O_3$ was synthesized in house using incipient wetness method. The powdered catalyst was ball-milled overnight and slurry dip-coated on foam metal until the desired loading was achieved. The coated catalyst was dried overnight and calcined at 350° C. for four hours.

In this experiment, two catalyst materials were used with exactly the same composition but in different physical form. Both catalyst materials had 15 wt % Co 1 wt % Ru/$\gamma$-$Al_2O_3$. One was in powder form tested in a micro fixed-bed reactor according to literature specification for minimizing the heat and mass transfer resistance. The other was a catalyst impregnated metal foam tested in a single channel testing unit.

Results are shown in Table E1-1. Even though both catalysts were tested under the identical conditions, powdered catalyst shows significantly higher conversion (99.6%) and higher selectivity to undesired product $CH_4$ (36%), apparently due to un-measured temperature excursions within catalyst bed.

TABLE E1-1

Fischer-Tropsch Catalyst Performance

| Catalyst | Conditions | Residence time | Conversion | $CH_4$ selectivity |
|---|---|---|---|---|
| Co—Ru/$Al_2O_3$/ foam | 231° C., 23-atm, $H_2$/CO = 3 | 1-sec | 17% | 9.6% |
| Co—Ru/$Al_2O_3$/ foam | 247° C., 23-atm, $H_2$/CO = 3 | 1-sec | 29% | 15% |
| Co—Ru/$Al_2O_3$/ foam | 264° C., 23-atm, $H_2$/CO = 3 | 1-sec | 50% | 22% |
| Co—Ru/$Al_2O_3$/ foam | 264° C., 23-atm, $H_2$/CO = 3 | 1-sec | 49% | 22% |
| Co—Ru/$Al_2O_3$/ foam | 275° C., 23-atm, $H_2$/CO = 3 | 1-sec | 69% | 24% |
| Co—Ru/$Al_2O_3$/ foam | 275° C., 23-atm, $H_2$/CO = 3 | 2-sec | 84% | 9.0% |
| Co—Ru/$Al_2O_3$/ foam | 245° C., 23 atm, $H_2$/CO = 3 | 1-sec | 33% | 12% |
| Co—Ru/$Al_2O_3$/ powder | 245° C., 23 atm, $H_2$/CO = 3 | 1-sec | 99.6% | 36% |

EXAMPLE 2

An experiment was conducted to demonstrate operation at various pressures. The equipment was the same as in Example 1.

According to the literature, variation in pressure should only affect true residence time in Fischer-Tropsch synthesis. In other words, conventional wisdom in Fischer-Tropsch reactions is that reaction rate is proportional to pressure under identical gas hourly space velocity (GHSV).

However, as shown in Table E2-1, with the catalyst structure of the present invention, catalyst activity was unexpectedly enhanced as the pressure was decreased under the same temperature and pressure corrected residence time. This surprising result is attributed to the enhanced mass and heat transfer possible with the catalyst structure of the present invention.

TABLE E2-1

Engineered catalyst performance for Fischer-Tropsch synthesis at 265° C. under a temperature and pressure corrected residence time of 12.5 seconds.

| Pressure, atm | Conversion, % | Selectivity to $CH_4$, % |
|---|---|---|
| 5 | 63 | 18 |
| 6 | 41 | 22 |
| 10 | 34 | 19 |
| 23 | 24 | 26 |

EXAMPLE 3

Use of Co or Ru alone as a catalyst on the metal foam was also tested under the conditions of Example 1 and performance was confirmed worse than that of bimetallic catalyst such as Co—Ru.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of conducting Fischer-Tropsch synthesis, comprising:
providing a microchannel reaction chamber comprising a catalyst for Fischer-Tropsch synthesis,
wherein the microchannel reaction chamber has at least one dimension of 8 mm or less;
passing a feed stream comprising a mixture of hydrogen and carbon monoxide gas through the microchannel reaction chamber with a residence time of about 1 second or less and at a temperature of 275° C. or less;
wherein the mixture comprises hydrogen and carbon monoxide in a ratio of from about 2:1 to about 3.5:1; and
converting at least 50% of the carbon monoxide in the mixture to hydrocarbons.

2. The method of claim 1 wherein the microchannel reaction chamber comprises at least one reaction chamber wall and wherein said at least one reaction chamber wall separates the reaction chamber from at least one cooling chamber.

3. The method of claim 2 wherein the microchannel reaction chamber has at least one dimension of 1 mm or less.

4. The method of claim 3 further comprising a methane selectivity of 24% or less.

5. The method of claim 1 wherein the catalyst comprises Co and Ru.

6. The method of claim 5 further comprising a methane selectivity of 24% or less.

7. The method of claim 6 wherein the catalyst comprises a metal foam support.

8. The method of claim 1 wherein the catalyst comprises a metal foam support.

9. The method of claim 1 wherein the temperature is in the range of 264 to 275° C.

10. The method of claim 9 further comprising a methane selectivity of 24% or less.

11. The method of claim 1 further comprising a methane selectivity of 24% or less.

12. The method of claim 2 wherein the temperature is in the range of 264 to 275° C.

13. The method of claim 2 wherein the catalyst comprises a metal foam support.

14. The method of claim 13 wherein the microchannel reaction chamber has at least one dimension of 1.5 mm or less.

15. The method of claim 12 wherein the microchannel reaction chamber has at least one dimension of 1.5 mm or less.

16. The method of claim 9 wherein the microchannel reaction chamber has at least one dimension of 1.5 mm or less.

17. A method of conducting Fischer-Tropsch synthesis, comprising:
providing a microchannel reaction chamber comprising a catalyst for Fischer-Tropsch synthesis,
wherein the microchannel reaction chamber has at least one dimension of 8 mm or less;
passing a feed stream comprising a mixture of hydrogen and carbon monoxide gas through the microchannel reaction chamber with a residence time of about 2 seconds or less and at a temperature of 275° C. or less;
wherein the mixture comprises hydrogen and carbon monoxide in a ratio of from about 2:1 to about 3.5:1; and
converting at least 50% of the carbon monoxide in the mixture to hydrocarbons.

18. The method of claim 17 wherein the microchannel reaction chamber comprises at least one reaction chamber wall and wherein said at least one reaction chamber wall separates the reaction chamber from at least one cooling chamber.

19. The method of claim 17 wherein the microchannel reaction chamber has at least one dimension of 1 mm or less.

20. The method of claim 18 wherein the catalyst comprises Co and Ru.

21. The method of claim 17 comprising converting at least about 80% of the carbon monoxide in the mixture to hydrocarbons.

22. The method of claim 18 comprising a selectivity to methane of no more than about 10%.

23. The method of claim 17 wherein the microchannel reaction chamber comprises a porous interfacial layer having a thickness of less than 50 microns.

24. The method of claim 3 wherein the microchannel reaction chamber comprises a porous interfacial layer having a thickness of less than 50 microns.

25. The method of claim 17 wherein the microchannel reaction chamber comprises a porous interfacial layer having a thickness of less than 20 microns.

26. The method of claim 3 wherein the microchannel reaction chamber comprises a porous interfacial layer having a thickness of less than 20 microns.

27. The method of claim 23 wherein the porous interfacial layer comprises a metal oxide impregnated with a catalyst metal selected from the group consisting of Fe, Co, Ru, Re, Os, and combinations thereof.

28. The method of claim 24 wherein the porous interfacial layer comprises a metal oxide impregnated with a catalyst metal selected from the group consisting of Fe, Co, Ru, Re, Os, and combinations thereof.

29. The method of claim 25 wherein the porous interfacial layer comprises a metal oxide impregnated with a catalyst metal selected from the group consisting of Fe, Co, Ru, Re, Os, and combinations thereof.

30. The method of claim 26 wherein the porous interfacial layer comprises a metal oxide impregnated with a catalyst metal selected from the group consisting of Fe, Co, Ru, Re, Os, and combinations thereof.

31. The method of claim 17 wherein the microchannel reaction chamber comprises a porous interfacial layer having a thickness of less than 20 microns.

32. A method of conducting Fischer-Tropsch synthesis, comprising:
   passing a feed stream comprising a mixture of hydrogen and carbon monoxide gas through a reaction chamber;
   wherein the microchannel reaction chamber has at least one dimension of 8 mm or less;
wherein the reaction chamber comprises catalyst structure comprising a porous interfacial layer having a thickness of less than 20 microns; and
   converting at least 50% of the carbon monoxide in the mixture to hydrocarbons.

33. The method of claim 32 wherein the catalyst structure comprises a first porous structure having a first pore size of at least about 0.1 μm and wherein the porous interfacial layer is disposed over the first porous structure and wherein the porous interfacial layer has a second pore size that is less than the first pore size; and
   further wherein the step of converting the carbon monoxide is conducted at a temperature of at least 200° C. and wherein the selectivity to methane is at most 25%.

34. The method of claim 33 wherein the porous interfacial layer comprises a metal oxide impregnated with a catalyst metal selected from the group consisting of Fe, Co, Ru, Re, Os, and combinations thereof.

35. The method of claim 32 wherein the reaction chamber comprises at least one reaction chamber wall and wherein said at least one reaction chamber wall separates the reaction chamber from at least one cooling chamber; and wherein the residence time of the mixture in the reaction channel is less than 5 seconds.

36. The method of claim 35 wherein the reaction chamber has at least one dimension of 1 mm or less.

37. The method of claim 34 wherein the reaction chamber has at least one dimension of 8 mm or less.

38. The method of claim 32 wherein the porous interfacial layer comprises a metal oxide impregnated with a catalyst metal selected from the group consisting of Fe, Co, Ru, Re, Os, and combinations thereof.

39. The method of claim 38 wherein the reaction chamber comprises at least one reaction chamber wall and wherein said at least one reaction chamber wall separates the reaction chamber from at least one cooling chamber; and wherein the residence time of the mixture in the reaction channel is less than 5 seconds.

40. The method of claim 35 wherein the reaction chamber has at least one dimension of 1 mm or less.

41. The method of claim 40 wherein the residence time of the mixture in the reaction channel is less than 2 seconds.

* * * * *